United States Patent [19]

Ramakrishna et al.

[11] Patent Number: 5,733,934
[45] Date of Patent: Mar. 31, 1998

[54] ANTIARRYTHMIC AND CARDIOPROTECTIVE SUBSTITUTED INDENOYLGUANIDINES

[75] Inventors: Nigrogi Venkata Satya Ramakrishna, Bombay; Tulsidas Sitaram More; Anagha Suhas Kulkarni, both of Thane; Bansi Lal, Bombay; Rao Venkata Satya Veerabhadra Vadlamudi, New Bombay; Anil Vasantrao Ghate, Thane; Ravindra Dattatraya Gupte, Bombay, all of India; Wolfgang Scholz, Eschborn; Hans Jochen Lang, Hofheim, both of Germany

[73] Assignee: Hoechst Aktiengesellschaft, Frankfurt am Main, Germany

[21] Appl. No.: 633,223

[22] Filed: Apr. 16, 1996

[51] Int. Cl.$^6$ .................. A01N 33/02; A01N 37/30
[52] U.S. Cl. .................. 514/634; 514/615; 564/74; 564/147; 564/237; 540/605; 544/330; 544/332; 548/330.1; 548/331.5; 548/332.5
[58] Field of Search .................. 548/330.1, 331.5, 548/332.5; 540/605; 544/330, 332; 564/74, 147, 237; 514/634

[56] References Cited

U.S. PATENT DOCUMENTS

| | | | |
|---|---|---|---|
| 2,734,904 | 2/1956 | Burtner | 260/295 |
| 3,780,027 | 12/1973 | Cragoe, Jr. et al. | 260/239.6 |
| 4,544,670 | 10/1985 | Studt et al. | 514/617 |

FOREIGN PATENT DOCUMENTS

WO 84/00875   3/1984   WIPO.

*Primary Examiner*—Mukund J. Shah
*Assistant Examiner*—Pavanaram K. Sripada
*Attorney, Agent, or Firm*—Finnegan, Henderson, Farabow, Garrett & Dunner, L.L.P.

[57] ABSTRACT

Indenoylguanidines of formula I and formula II, the process for their preparation, their use as medicaments, medicaments containing them, their use as diagnostic agents and medicaments containing them are described. Compounds I are useful for treating cardiac arrhythmias. Further they are useful as cardioprotective agents in mammals, which comprises administering the compound of formula-I or II with the above properties in combination with pharmaceutically accepted carrier to said mammal.

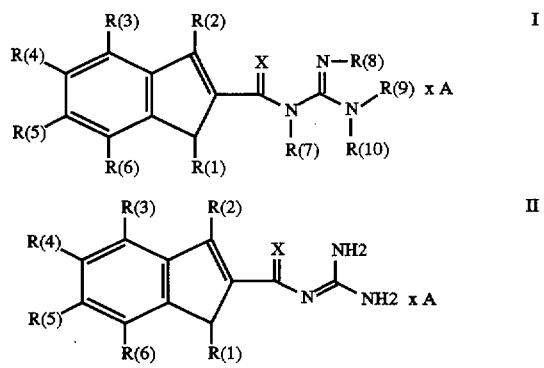

17 Claims, No Drawings

ANTIARRYTHMIC AND CARDIOPROTECTIVE SUBSTITUTED INDENOYLGUANIDINES

The invention relates to indenoylguanidines, a process for their preparation, their use as medicaments, their use as diagnostic agents and medicaments containing them. More particularly, the present invention relates to the indenoylguanidines having the formula I

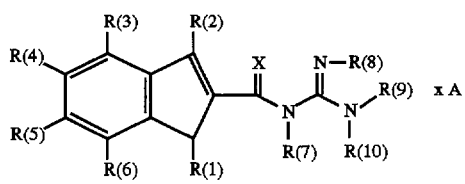

wherein
R(1) and R(2) are individually or collectively hydrogen, alkyl having 1, 2, 3, 4, 5, 6, 7, 8, 9 or 10 carbon atoms; cycloalkyl having 3, 4, 5 or 6 carbon atoms, O—C(=O)-alkyl having 1, 2, 3 or 4 carbon atoms, O—C(=O)-alkyl having 1, 2, 3 or 4 carbon atoms, $C_mH_{2m}$-NR (12)R(13), wherein R(12) and R(13) are independently from each other hydrogen or alkyl having 1, 2, 3 or 4 carbon atoms; m is zero, 2, 3 or 4;

NH—C(=O)—NH$_2$, C(=O)—O-alkyl having 1, 2, 3 or 4 carbon atoms, C(=O)—NH$_2$, C(=O)—NH-alkyl having 1, 2, 3 or 4 carbon atoms, C(=O)-N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenyl-aryl having 2, 3, 4, 5, 6, 7, 8, 9 or 10 carbon atoms in the alkenyl group, alkynyl-aryl having 2, 3, 4, 5, 6, 7, 8, 9 or 10 carbon atoms in the alkynyl group, $C_1$-$C_4$-alkyl-substituted-aryl, $C_1$-$C_4$-alkyl-heteroaryl, $C_1$-$C_4$-alkenyl-heteroaryl, aminoalkyl-aryl having 1, 2, 3 or 4 carbon atoms in the alkyl group, substituted-aryl, heteroaryl and substituted heteroaryl;

R(3), R(4), R(5) and R(6) are individually or collectively hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogens (such as F, Cl, Br, I) , OH, aryl, substituted aryl, heteroaryl, substituted heteroaryl, O-lower alkyl, O-aryl, O-lower alkyl aryl, O-substituted aryl, O-lower alkyl-substituted aryl, O—C(=O)-$C_1$-$C_4$-Alkyl-aryl, O—C(=O)—NH—$C_1$-$C_4$-alkyl, O—C(=O)—N($C_1$-$C_4$-alkyl)$_2$, NO$_2$, CN, CF$_3$, NH$_2$, NH—C(=O)-$C_1$-$C_4$-alkyl, NH—C(=O)—NH$_2$, COOH, C(=O)—O—$C_1$-$C_4$-alkyl, C(=O)—NH$_2$, C(=O—NH—$C_1$-$C_4$-alkyl, C(=O)—N($C_1$-$C_4$-alkyl)$_2$, $C_1$-$C_4$-COOH, $C_1$-$C_4$-alkyl-C(=O)—O—$C_1$-$C_4$-alkyl, SO$_3$H, SO$_2$alkyl, SO$_2$-alkylaryl, SO$_2$—N—(alkyl)$_2$, SO$_2$-N(alkyl)(alkylaryl), C(=O)—R(11), $C_1$-$C_{10}$-alkyl-C(=O)—R (11), $C_2$-$C_{10}$-alkenyl-C(=O)—R(11), $C_2$-$C_{10}$-alkynyl-C(=O)—R(11), NH—C(=O)—$C_1$-$C_{10}$-alkyl-C(=O)—R(11), O—$C_1$-$C_{11}$-alkyl-C(=O)—R (11), wherein R(11) is $C_1$-$C_4$-alkyl, $C_1$-$C_4$-alkynyl, aryl substituted aryl, NH$_2$, NH-$C_1$-$C_4$-alkyl, N-($C_1$-$C_4$-alkyl)$_2$, SO$_3$H, SO$_2$alkyl, SO$_2$-alkylaryl, SO$_2$-N-(alkyl)$_2$, SO$_2$-N(alkyl) (alkylaryl);

X is O, S or NH;
R(7), R(8), R(9) and R(10) are individually or collectively hydrogen, alkyl, cycloalkyl, aryl, alkylaryl;

or

R(8) and R(9)

together may be the part of a 5, 6 or 7-membered heterocyclic ring;

A is absent or a nontoxic organic or mineral acid.

Exemplary acids are hydrochloric acid, hydrobromic acid, sulfuric acid, nitric acid, phosphoric acid, methanesulfonic acid, benzene sulfonic acid, toluene sulfonic acid, acetic acid, lactic acid, salicyclic acid, benzoic acid, nicotinic acid, phthalic acid, stearic acid, oleic acid and oxalic acid.

Throughout this disclosure, the following terms, unless otherwise indicated, shall be understood to have the following meanings:

"Alkyl" means a saturated aliphatic hydrocarbon which may be either straight or branched-chain. Preferred alkyl groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to about 6 carbon atoms. Examples of lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group. Preferred groups have about 3 to about 6 carbon atoms, and exemplary groups include cyclopropyl, cyclopentyl and cyclohexyl.

"Alkenyl" means an unsaturated aliphatic hydrocarbon. Preferred groups have no more than about 12 carbon atoms. Exemplary groups include any structural and geometric isomers of ethenyl, propenyl, butenyl, pentenyl, hexenyl, heptenyl, octenyl, nonenyl, decenyl, undecenyl and dodecenyl or butadienyl, pentadienyl etc., "Lower alkenyl" means alkenyl of about 2 to 6 carbon atoms. Preferred groups include ethenyl, propenyl, butenyl, isobutenyl, and all structural and geometrical isomers thereof.

"Alkynyl" means an unsaturated aliphatic hydrocarbon. Preferred groups have no more than about 12 carbon atoms and contain one or more triple bonds, including any structural or isomers of ethynyl, propynyl, butynyl, pentynyl, hexynyl, heptynyl, octynyl, nonynyl, decynyl, undecynyl, dodecynyl, etc.

"Lower alkynyl" means alkynyl of about 2 to 6 carbon atoms. Preferred groups include structural isomers of propynyl, butynyl, and pentynyl.

"Aryl" means phenyl and substituted phenyl.

"Substituted Phenyl" means a phenyl group in which one or more of the hydrogens have been replaced by the same or different substituents including halogen, lower alkyl, lower alkenyl, lower alkynyl, halo-lower alkyl, nitro, amino, acylamino, hydroxy, carboxyl, lower alkoxy, aryl lower alkoxy, acyloxy lower alkanoyl, cyano, amido, loweralkylamino, lower alkoxyamino, aralkylamino, or loweralkylsulfonyl.

"Aralkyl" means an alkyl group in which one or more hydrogens have been substituted by an aryl group. Preferred groups are phenalkyl and substituted phenalkyl.

"Phenalkyl" means an alkyl group substituted by a phenyl group.

"Substituted phenalkyl" means a phenalkyl group in which one or more phenyl hydrogen are replaced as given above with respect to substituted phenyl.

"Substituted phenalkenyl" mean a phenalkenyl group in which the phenyl group is substituted as given above with respect to substituted phenyl.

"Heterocyclic ring" or "heterocycle" means a 3, 5, 6 or 7 membered ring having 1 to 3 hetero atoms which may be nitrogen, oxygen or sulfur, including pyrrole, pyrrolidine, pyridone, heptamethyleneiminyl, pyrazole, pyridyl, pyrimidyl, pyrazolyl, imidazolyl, isoxazolyl, furyl, thienyl, oxazolyl, thiazolyl, piperidyl, morpholinyl, oxazolidinyl, thiazolidinyl, pyrazolidinyl, imidazolidinyl, piperazinyl, thiamorpholinyl, azepinyl and ethyleneiminyl.

"Substituted heterocycle" means a heterocycle in which one or more of the hydrogens on the ring carbons have been replaced by substituents as given above with respect to substituted phenyl.

The term "halo" and "halogen" include all four halogens; namely fluorine, chlorine, bromine and iodine. The halo alkyls, halophenyl and halo-substituted pyridyl groups having more than one halo substituent which may be the same or different such as trifluoromethyl, 1-chloro-2-bromo-ethyl, chlorophenyl, and 4-chloropyridyl.

"Acyl" means an organic carbonyl radical of a lower alkanoic acid. Preferred acyl groups are lower alkanoyl groups such as acetyl and propionyl.

"Aroyl" means an aromatic acid radical such as benzoyl, toluoyl.

"Lower alkanoyl" means the acyl radical of a lower alkanoic acid such as acetyl, propionyl, butyryl, valeryl, stearoyl and the like.

"Alkoxy" means an alkyloxy group and includes hydroxy alkyl groups. Preferred lower alkoxy groups are methoxy, ethoxy, n-propoxy and isopropoxy, isobutoxy, n-butoxy and t-butoxy.

Nontoxic organic or mineral acids A forming the addition salts are for example hydrochloric acid, hydrobromic acid, sulfuric acid, nitric acid, phosphoric acid, methanesulfonic acid, benzene sulfonic acid, acetic acid, lactic acid, salicyclic acid, benzoic acid, nicotinic acid, phthalic acid, stearic acid, oleic acid and oxalic acid.

Preferred compounds of the invention are compounds of formula II

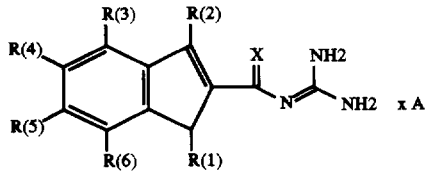

wherein
R(1) is hydrogen, $C_1$–$C_4$-alkyl, NR(12)R(13) wherein
  R(12) and R(13) are independently from each other hydrogen or alkyl having 1, 2, 3 or 4 carbon atoms, $C_1$–$C_4$-alkyl-$NH_2$, aryl-alkyl-$NH_2$, O-alkyl, C(=O)—NH(lower alkyl), C(=O)—N(lower alkyl)$_2$, C(=O)—O—lower alkyl, substituted alkyl, aryl, substituted aryl;
R(2) is hydrogen, $C_1$–$C_4$-alkyl, $C_1$–$C_4$-alkyl-$NH_2$, aryl-alkyl-$NH_2$, substituted alkyl, aryl, substituted aryl;
R(3), R(4), R(5) and R(6) are
  individually or collectively F, Cl, Br, I, OH, O-lower alkyl, O-aryl, O-lower alkyl-aryl, O-substituted aryl, O-lower alkyl-substituted aryl, COOH, C(=O)—O-lower alkyl, CN, $CF_3$, $NH_2$, NH-lower alkyl, N(lower alkyl)$_2$, O-lower alkyl-$NH_2$, O-lower alkyl-NH(lower alkyl), O-lower alkyl-N(lower alkyl)$_2$, $SO_2$-lower alkyl, $SO_3H$, $SO_2$—$NH_2$, $SO_2$-NH-lower alkyl, $SO_2$-N(lower alkyl)$_2$, heteroaryl, substituted heteroaryl;
  the preferred groups for heteroaryl being pyridyl, thienyl, furyl, quinyl and isoquinyl;
  the preferred substituents for substituted heteroaryl being F, Cl, Br, I, OH, $NH_2$, O-lower alkyl, O-lower alkyl-aryl, COOH, C(=O)—O-lower alkyl, CN, NH-lower alkyl, N(lower alkyl)$_2$ $SO_3H$, $SO_2$—$NH_2$, $SO_2$—NH-lower alkyl, $SO_2$—N(lower alkyl)$_2$;
X is O, S or NH, but preferably X is O;
A is absent or a nontoxic organic or mineral acid.

The compounds of the present invention may contain asymmetric centres, the invention relates to both compounds of the S and of the R configuration. The compounds can exist as optical isomers, as racemates or as mixtures thereof.

Representative examples of the compounds of this invention are listed in Table 1 and Table 2.

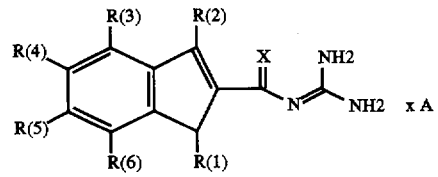

wherein
R(1) and R(3) are H
R(2) is $CH_3$;
X is O
in formula II

TABLE 1

| Compound No. | R(4) | R(5) | R(6) | A | M.P. °C. |
|---|---|---|---|---|---|
| 1. | H | H | H | HCl | 250–251 |
| 2. | H | H | H | $CH_3SO_3H$ | 226–227 |
| 3. | F | H | H | HCl | 230–231 |
| 4. | F | H | H | $CH_3SO_3H$ | 243–244 |
| 5. | Cl | H | H | $CH_3SO_3H$ | 210–212 |
| 6. | Br | H | H | $CH_3SO_3H$ | 230–231 |
| 7. | I | H | H | $CH_3SO_3H$ | 215–216 |
| 8. | $C_5H_{10}NSO_2$ | H | H | $CH_3SO_3H$ | 220–221 |
| 9. | H | Cl | H | $CH_3SO_3H$ | 198–199 |
| 10. | H | H | Cl | $CH_3SO_3H$ | 180–181 |
| 11. | H | H | Br | $CH_3SO_3H$ | 225–226 |
| 12. | H | H | I | $CH_3SO_3H$ | 235–236 |

TABLE 2 wherein
R(1), R(2) and R(3) are H;
X is O
in formula II

| Compound No. | R(4) | R(5) | R(6) | A | M.P. °C. |
|---|---|---|---|---|---|
| 13. | H | H | H | $CH_3SO_3H$ | 164–165 |
| 14. | H | H | $CH_3$ | $CH_3SO_3H$ | 198–200 |

TABLE 3 wherein X = O and A = $CH_3SO_3H$

| Compound No. | R(1) | R(2) | R(3) | R(4) | R(5) | R(6) | M.P. °C. |
|---|---|---|---|---|---|---|---|
| 15. | H | $CH_3$ | H | H | Br | H | 125–126 |
| 16. | H | $CH_3$ | H | H | F | H | 235–236 |
| 17. | H | $CH_3$ | H | H | H | $CH_3$ | 215–216 |
| 18. | H | $CH_3$ | H | $CH_3$ | H | H | 225–226 |
| 19. | H | $CH_3$ | H | H | $CH_3$ | H | 215–216 |
| 20. | H | $CH_3$ | H | $CH_3$ | H | $CH_3$ | 210–211 |
| 21. | H | $CH_3$ | H | H | I | H | 175–176 |
| 22. | H | H | H | $CH_3$ | H | H | 220–221 |
| 23. | H | H | $CH_3$ | H | H | H | 225–226 |
| 24. | H | H | $CH_3$ | H | H | $CH_3$ | 230–231 |

TABLE 3-continued wherein X = O and A = CH$_3$SO$_3$H

| Compound No. | R(1) | R(2) | R(3) | R(4) | R(5) | R(6) | M.P. °C. |
|---|---|---|---|---|---|---|---|
| 25. | H | H | H | CH$_3$ | H | CH$_3$ | 215–216 |
| 26. | H | H | H | H | CH$_3$ | H | 215–216 |
| 27. | H | CH$_3$ | Cl | Cl | H | H | 148–149 |
| 28. | H | CH$_3$ | CH$_3$ | H | H | CH$_3$ | 195–196 |
| 29. | CH$_3$ | CH$_3$ | H | H | H | H | 195–196 |
| 30. | OCH$_3$ | CH$_3$ | H | H | H | H | 188–190 |

The compounds of formula-I are substituted acylguanidines. The most prominent representatives of the acylguanidines is the pyrazine derivative amiloride, which is used in therapy as a potassium-saving diuretic. Numerous other compounds of the amiloride type are described in the literature, such as, for example, dimethylamiloride or ethylisopropylamiloride.

Studies which indicate antiarrhythmic properties of amiloride moreover have been disclosed [Circulation 79, 1257–1263 (1989)]. However, wide use as an antiarrhythmic is impeded by the fact that this effect is only slight and occurs accompanied by an antihypertensive and salutetic action and these side effects are undesirable in the treatment of disturbances in cardiac rhythm.

Indications of antiarrhythmic properties of amiloride have also been obtained from experiments on isolated animal hearts [Eur. Heart J. 9 {supplement 1}: 167 (1988) (book of abstracts)]. Thus, for example, it has been found on rat hearts that it was possible to suppress an artificially induced ventricular fibrillation completely by amiloride. The above mentioned amiloride derivative ethylisopropylamiloride was even more potent than amiloride in this model.

Benzoylguanidines having antiarrhythmic properties are described in European specification No 416 499 laid open to public inspection.

U.S. Pat. No. 3,780,027 describes acylguanidines, which differ fundamentally from the compounds of formula-I according to the invention described here in that they are trisubstituted benzoylguanidines which are derived in their substitution pattern from commercially available diuretics, such as bumetanide and furosemide and have an amino group, which is important for the salidiuretic action sought, in position 2 or 3 relative to the carbonylguanidine group. A potent salidiuretic activity is correspondingly reported for these compounds.

Circulation 79, 1257–1263 discloses antiarrhythmic properties of amiloride—a molecule containing an acylguanidine unit. U.S. Pat. Nos. 3,780,027 and 4,544,670, and 2,734,904 also disclose acylguanidines. These documents relate to acylguanidines wherein the heterocyclic (Circulation 79,1257–1263) or phenyl (U.S. Pat. Nos. 3,780,027, 2,734, 904 and 4,544,670) residue is attached to the acylguanidine unit.

In the present invention the heterocyclic or aromatic residue is separated from the acylguanidine unit by an ethylenic bond in trans geometry in the form of a five-membered carbocyclic ring. It is found that these compounds have very good antiarrhythmic properties.

These compounds have considerable advantage over currently available antiarrhythmic pharmaceuticals and are useful as cardioprotective compounds for infarct treatment and also for the treatment of angina pectoris.

It was surprising that the compounds according to the invention have no undesirable and adverse salidiuretic properties but very good antiarrhythmic properties, so they can be used for the treatment of health disorders, such as oxygen deficiency symptoms. As the result of their pharmacological properties, the compounds are outstandingly suitable as antiarrhythmic medicaments having a cardioprotective component and for prophylaxis of infarction and for treatment of angina pectoris, where they also preventively inhibit or greatly reduce the pathophysiological processes in the development of ischemically induced damage, in particular the initiation of ischemically induced cardiac arrhythmias. Because of their protective actions against pathological hypoxic and ischemic situation, the compounds of the formula I according to the invention, as a result of inhibition of the cellular Na$^+$/H$^+$ exchange mechanism, can be used as medicaments for the treatment of all acute or chronic damage caused by ischemia or diseases thereby induced primarily or secondarily. This applies to their use as medicaments for surgical interventions, for example organ transplants, where the compounds can be used both for protection of the organs in the donor before and during removal, for protection of organs removed, for example during treatment with or storage thereof in physiological bath fluids, and also during transfer to the recipient organism. The compounds are also valuable medicaments which have a protective action while angioplastic surgical interventions are carried out, for example on the heart and also on peripheral vessels. In accordance with their protective action against ischemically induced damage, the compounds are also suitable as medicaments for the treatment of ischemias of the nervous system, in particular the CNS, where they are suitable, for example, for the treatment of apoplexy or cerebral edema. The compounds of the formula-I according to the invention moreover are also suitable for treatments of forms of shock, such as, for example, allergic, cardiogenic, hypovolemic and bacterial shock.

The compounds of formula I according to the invention furthermore are distinguished by a potent inhibiting action on the proliferations of cells, for example fibroblast cell proliferation and proliferation of smooth vascular muscle cells. The compounds of the formula-I are therefore possible valuable therapeutics for diseases in which cell proliferation is a primary or secondary cause, and they can therefore be used as antiatherosclerotics and as agents delayed diabetic complications, cancer diseases, fibrotic diseases, such as pulmonary fibrosis, hepatic fibrosis or renal fibrosis, and organ hypertrophies and hyperplasias, in particular prostate hyperplasia or prostate hypertrophy.

The compounds according to the invention are effective inhibitors of the cellular sodium/proton antiport (Na$^+$/H$^+$ exchanger), which, in numerous diseases (essential hypertension, atherosclerosis, diabetes and the like) is also increased in those cells which are readily accessible for measurements, such as, for example, in erythrocytes, platelets or leukocytes. The compounds according to the invention are therefore suitable as outstanding and simple scientific tools, for example in their use as diagnostics for determination and differentiation of certain forms of hypertension, but also of atherosclerosis, diabetes, proliferative diseases and the like. The compounds of the formula I furthermore are suitable for preventive therapy for prevention of the origin of high blood pressure, for example essential hypertension.

This invention also relates to the process for preparation of compounds of formula I. The preparation of the compounds of the invention are illustrated, but not limited, by preparation of exemplary compounds of the invention.

The synthesis of compounds of formula I, when R(2) is not H, was achieved through intermediate of formula III,

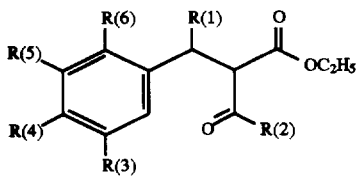

which in turn are made through methods known to men of art in synthesis. One of the methods is by generating the anion on activated methylene by NaH/THF followed by alkylation using substituted benzylbromides. Compounds of formula III are converted into 3-substituted-indene-2-carboxylic acids of formula IV on treatment with concentrated sulfuric acid at room temperature in 10–12 hours and subsequent aqueous work-up.

The synthesis of compounds of formula I, when R(2)=H, was achieved through the intermediate of formula V,

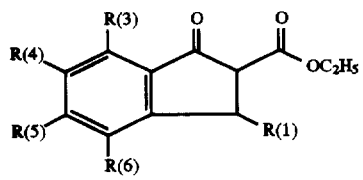

which in turn are made through methods known to men of art in synthesis. One of the methods is by generating the anion on the activated methylene next to carbonyl group using butyl lithium followed by acylation using ethyl chloroformate. Alternatively same product can be achieved Using the method of enamine acylation of carbonyl compounds. Compounds of formula V are converted into indene-2-carboxylic acids of formula IV

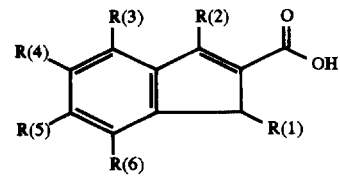

on reduction of carbonyl group by sodium borohydride followed by acid catalyzed (p-toluenesulfonic acid) dehydration in dry benzene.

Values of R(1), R(2), R(3), R(4), R(5) and R(6) for formula III, IV and formula VI

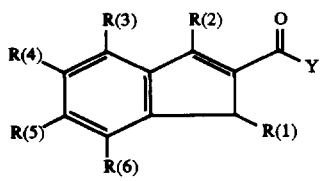

have same meaning as have been defined for formula I. For formula V R(1), R(3), R(4), R(5) and R(6) have same values as have been defined for formula I. The invention also relates to a process for the preparation of compounds of formula I, which comprises of reacting compounds of formula VI with a free guanidine or with a compound of formula VII

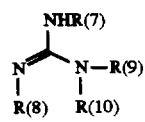

in which R(7), R(8), R(9) and R(10) have values as defined earlier in formula I and Y is a leaving group which can be easily displaced by a nucleophile.

The activated acid derivatives of the formula VI in which Y is an alkoxy group, preferably a methoxy group, an activated phenoxy group, a phenylthio, methylthio, 2-pyridylthio group or a nitrogen heterocycle, such as imidazolyl, which can be prepared from acid chloride (formula VI; Y=Cl) which in turn can be prepared from acid, formula-IV on treatment with thionyl chloride. Other activating ester methods can be used, which are known in peptide area to activate the acid for coupling reaction. The imidazolides of formula VI, Y=imidazolides, can also be prepared from a compound of formula IV, by treating it with 1,1-carbonyldiimidazole [C.Staab, Angew. Chem. Int. Eng Edn. 351–367 (1962)]. Compound of formula VI (Y=Cl) on treatment with the compound of formula VII under Schotten-Baumann condition, also gives compound of formula I. Other mixed anhydride related to formula VI may be prepared, such as with ClCOOEt, tosyl chloride, triethylphosphoryl chloride in the presence of triethylamine or any other base in an inert solvent. Activation of the COOH group in the compounds of the formula IV can also be achieved with DCC. Other methods of preparation of activated carboxylic acid derivative of formula VI type are given with indication of source lit. in J.March, Advanced Organic Chemistry, 3rd Edition (John Wiley & Son, 1985), p. 350. Coupling reaction between compounds of formula VI and VII can be conducted in variety of ways in protic or aprotic polar solvents, but inert organic solvents are preferred. In this connection methanol, THF, DMF, N-methylpyrrolidone, HMPA etc., between room temperature and boiling point of these solvents have proved suitable for the reaction of the formula VI (Y=OMe) with guanidine. Reaction of compounds of formula VI with salt free guanidine are advantageously carried out in aprotic inert solvents such as THF, dimethoxy ethane, DMF or dioxane. In case where compound of formula IV is directly treated with carbonyldiimidazole for activating the carboxy group, aprotic polar solvents such as DMF, dimethoxy ethane are used, followed by the addition of compound of formula VII. Compounds of the formula I may be converted into pharmacologically acceptable acid addition salts with exemplary salts as described earlier in this disclosure.

The active compounds of the present invention may be administered orally, parenterally, intravenously, rectally or by inhalation, the preferred administration being dependent on the specific clinical need of the disorder. In this connection, the compounds of formula-I can also be used alone or together with pharmaceutical auxiliaries, and indeed both in veterinary and in human medicine. Which auxiliaries are suitable for the desired pharmaceutical formulation or composition is familiar to the person skilled in the art on the basis of his expert knowledge. In addition to solvents, gel-forming agents, suppository bases, tablet auxiliaries and other active compound carriers, antioxidants, dispersants, emulsifiers, defoaming agents, flavor correctors, preservatives, solubilizers or colorants can be used.

For a form for oral use, the active compounds are mixed with the additives suitable for this purpose, such as excipients, stabilizers or inert diluents and are brought into the forms suitable of administration, such as tablets, coated tablets, hard gelatin capsules, aqueous, alcoholic or oily solutions, by the customary methods. Inert carriers which can be used are, for example, gum arabic, magnesia, magnesium carbonate, potassium phosphate, lactose, glucose or starch, in particular corn starch. In this case, preparation can take place both as dry and as moist granules. Suitable oily excipients or solvents are, for .example, vegetable or animal oils, such as sunflower oil or cod liver oil.

For subcutaneous or intravenous administration, the active compounds, if desired with the substances customary for this purpose such as solubilizers, emulsifiers or other auxiliaries, are brought into solution, suspension or emulsion. Possible solvents are, for example: water, physiological saline solution or alcohols, for example ethanol, propanol, glycerol, in addition also sugar solutions such as glucose or mannitol solutions, or alternatively, a mixture of the various solvents mentioned.

Pharmaceutical formulations suitable for administration in the form of aerosols or sprays are, for example, solutions, suspensions or emulsions of the active compound of formula I in a pharmaceutically acceptable solvent, such as, in particular, ethanol or water, or a mixture of such solvents. If required, the formulation may also contain other pharmaceutical auxiliaries such as surfactants, emulsifiers and stabilizers and also a propellant gas. Such a preparation customarily contains the active compound in a concentration of about 0.1 to 10, in particular of about 0.3 to 3% by weight.

The dosage of the active compound of the formula-I to be administered and the frequency of administration depend on the potency and duration of action of the compounds used; and additionally also on the nature and severity of the disease to be treated and on the sex, age, weight and individual responsiveness of the mammal to be treated.

On an average, the daily dose of a compound of the formula I in a patient of about 75 kg weight is at least 0.001 mg, preferably 0.01 mg to at most 10 mg, preferably at most 1.0 mg per kg of weight. In acute outbreaks of the illness, for example immediately after suffering a cardiac infarction, still higher and above all, more frequent dosages may also be necessary, for example up to 4 individual doses per day. In particular on i.v use, for example in an infarct patient in the intensive care unit, up to 100 mg per day may be necessary.

EXPERIMENTAL SECTION

The synthesis of representative examples, 3-methylindene-2-oylguanidine-monohydrochloride (compound No. 1 of formula I in Table 1) and Indene-2-oylguanidine-methanesulfonic acid (compound no. 13 of formula I in Table-2) are described, other compounds were also synthesized using such/other sequences.

A. Synthesis of Compound No 1 in Table 1:

a. Synthesis of compounds with formula III:

NaH (13.8 g, 0.6 mole) was washed twice with hexane (2×50 ml) and suspended in 250 ml of freshly distilled THF. Next ethyl acetoacetate (75 ml, excess) was added dropwise carefully while the receiving flask was cooled at −10° C. After the addition was complete, it was stirred at −10° C. for 2 hours and at room temperature for 30 min. Benzylbromide (51.0 g, 0.3 mole) in THF was added dropwise at room temperature to the above solution. The reaction mixture was stirred overnight at room temperature. The reaction was terminated the next day by pouring into ice cold water, brought to neutral pH, and extracted with ether/ethylacetate. The combined ether/ethylacetate extracts were rinsed over brine and dried over $Na_2SO_4$. Removal of the solvent followed by careful vacuum distillation gave ethyl-benzylacetoacetate, bp 276° C. IR: (neat), $cm^{-1}$: 2900–3050, 1690–1760 (broad), 1655. NMR: $(CDCl_3):\delta:1.25$ ($t_1$ 3H, $CH_2CH_3$); 2.25 (s, 3H, $COCH_3$); 3.20 (d, 2H, benzylic $CH_2$); 3.8 (t, 1H, COCHCO); 4.20 (q, 2H, $OCH_2CH_3$); 7.15–7.35 (m, 5H, Ar-H).

b. Synthesis of Compounds with formula IV:

Ethyl-benzylacetoacetate (37 g) was added to a mixture of sulphuric acid (98%, 360 g) and water (15 g) cooled to −2° C. during 45 min, under vigorous stirring. The solution, now dark reddish brown, was stirred at 4° C. for 2 hours and then overnight at 15°–20° C., it was then poured into ice-water (2.0 l). This mixture was heated to 50.60° C. to coagulate the sludge and was then filtered and worked up. The 3-methylindene-2-carboxylic acid was purified by column chromatography followed by recrystallization, mp 200° C. IR: (KBr), $cm^{-1}$:2900–3100 (broad), 1640–1680, 1600. NMR: $(CDCl_3):\delta:2.45$ (s, 3H, $CH_3$); 3.55 (s, 2H, $CH_2$); 7.20–7.40 (m, 4H, Ar-H).

| Analysis: | C % | H % |
| --- | --- | --- |
| Calcd. for $C_{11}H_{10}O_2$: | 76.99 | 5.79 |
| Found: | 76.43 | 5.86 | c. Synthesis of Compounds with formula I:

1.0 g of 3-methylindene-2-carboxylic acid and 5 ml thionyl chloride were refluxed for 4 hours. Careful removal of the solvent by distillation under reduced pressure gave 3-methylindene-2-oyl chloride. The acid chloride dissolved in THF was dropped into a mixture of guanidine and sodium hydroxide at room temperature over a period of 10 min. and stirred for one hour. The reaction was terminated by work-up and the product was purified by column chromatography.

3-Methylindene-2-oylguanidine-monohydrochloride was obtained by dissolving the free base in methanol followed by adding ethereal HCl up to pH 2.0 and stirring. The salt was precipitated out with cooling in an ice-bath. White crystalline powder, mp 250°–251° C. IR: (KBr), $cm^{-1}$: 3100–3350 (broad); 1690, 1655. NMR: $(CDCl_3):\delta:2.45$ (s, 3H, $CH_3$); 4.0 (s, 2H, $CH_2$); 7.4–7.7 (m, 4H, Ar-H); 8.4 (bs, 2H, $NH_2$, exchangeable with $D_2O$)

| Analysis: | C % | H % | N % | Cl % |
| --- | --- | --- | --- | --- |
| Calcd. for $C_{12}H_{16}O_2N_3Cl$: | 53.42 | 5.90 | 15.57 | 13.16 |
| Found: | 53.12 | 5.42 | 15.94 | 13.68 |

B. Synthesis of Compound No 13 in Table 2:

d. Synthesis of Compounds with formula V:

1-Indanone (1.5 g, 11.36 mmols) was dissolved in dry THF in a three neck flask equipped with nitrogen inlet, septum and a guard tube. The flask was cooled to −20° C. for 10 minutes. Then butyl lithium (11.37 ml, 12.48 mmols) was added dropwise through the septum using the syringe. The reaction mixture was allowed to stand at −20° C. for 45 minutes and then ethyl chloroformate (1.08 ml, 10 mmols) was added dropwise using a syringe. The reaction mixture was stirred at −20° C. for 30 minutes and slowly brought to room temperature in about one hour. The reaction was worked-up by evaporating the THF and the product was chromatographed to yield 2-carbethoxy-1-indanone. NMR: $(CDCl_3):\delta:1.25$ (t, 3H, $OCH_2CH_3$); 3.45 (d, 2H, benzylic $CH_2$); 3.65 (t, 1H, COCHCO); 4.2 (q, 2H, $OCH_2CH_3$); 7.4–7.5 (m, 4H, Ar-H).

e. Synthesis of compounds with formula IV:

2-Carbethoxy-1-indanone was dissolved in dry methanol at room temperature, to which sodium borohydride was added in three lots while the reaction mixture was kept stirring. The reaction mixture was further stirred for 30 minutes, after which the solid was filtered and the filtrate was evaporated to dryness. The residue was dissolved in dry benzene, to which catalytic amount of p-toluenesulfonic acid was added and the reaction mixture was stirred for one hour. The p-toluenesulfonic acid was filtered off and the filtrate was concentrated to yield ethyl indene-2-carboxylate. The ethyl indene-2-carboxylate was dissolved in methanol and 1.0 equivalent of aqueous sodium hydroxide solution was added and the reaction mixture was kept stirring for overnight. The next day, the reaction was terminated by evaporating the methanol, followed by diluting the residue with water, brought to neutral pH and the precipitated indene-2-carboxylic acid was filtered. NMR: ($CDCl_3$): $\delta$:3.75 (s, 2H, benzylic $CH_2$); 7.4–7.7 (m, 4H, Ar-H); 7.95 (s, 1H, olefinic H).

f. Synthesis of compounds of formula I:

The same procedure described earlier in experimental section-A-c for the preparation of compound No 1 was followed for the synthesis of compound 13 in table 2 from indene-2-carboxylic acid.

Indene-2-oylguanidine-methanesulfonic acid was obtained by dissolving the free base in ethyl acetate at room temperatue followed by addition of methanesulfonic acid (1 eq). The salt was precipitated out with cooling in an ice-bath. Yellow crystalline powder, mp 164°–165° C. NMR: ($CDCl_3$):$\delta$:3.75 (S, 2H, benzylic $CH_2$); 7.4–7.7 (m, 4H, Ar-H); 8.05 (s, 1H, olefinic H); 8.35 and 11.09 (bs, NH and $NH_2$, exchangeable with $D_2O$).

Pharmacological methods to evaluate Antiarrhythmic and Cardioprotective action:

Sodium-Proton exchange inhibition in rabbit erythrocytes:

Albino rabbits of New Zealand strain were fed with 2% cholesterol diet for six weeks prior to collecting blood for the determination of $Na^+/H^+$-exchanger activity in the erythrocytes. Eypercholesteremia has been reported to increase the exchanger activity in the rabbit erythrocytes (Scholz et al, 1990; Arteriosklerose—Neue Aspekte aus Zellbiologie und Molekulargenetik, Epidemiologie und Klinik; Assmann, G, et al, Eds. Braunschweig, Wiesbaden, Vieweg, 296–302). Blood samples were collected from the ear vein and hematocrit was determined. About 200 µl of blood was incubated at 37° C. for 1 hour with hyperosmolar sucrose buffer containing 0.1 mM Ouabain in the presence and absence of test sample. After the incubation period, the reaction was stopped by addition of 5 ml of ice cold $MgCl_2$ solution containing 0.1 mM Ouabain. The erythrocytes were washed three times with 5 ml quantities of $MgCl_2$ solution. They were hemolyzed by the addition of 4 ml of distilled water and the sodium content of the hemolyzed was determined by flame-photometry. The activity of the test compound was determined by its ability to reduce the sodium content of the erythrocyte and was expressed as $IC_{50}$ which is the concentration necessary to reduce the erythrocyte sodium content to 50%.

| Compound No. | $IC_{50}$(µM) |
|---|---|
| 2 | 0.09 |
| 10 | 0.018 |

Reperfusion Induced Arrhythmias in the isolated rat heart:

Male Charles Foster rats of either sex (250–300 g) were sacrificed by stunning and exsanguination. Hearts were quickly removed and perfused according to Langendorffs method. Different concentrations of test compound were added into the perfusing medium. After 20 min of the equilibration period Left Anterior Descending (LAD) coronary artery was ligated. 15 minutes later the ligature was removed and reperfusion was allowed for next 30 minutes. During reperfusion period ECG was monitored. Duration of Ventricular Fibrillation (VFD) was the main parameter of assessment. Anti-arrhythmic activity was examined as the concentration of the test compound required to cause a 50% reduction of the VFD.

TABLE 5

| Compound No. | $IC_{50}$ for VFD |
|---|---|
| 2 | 0.025 µM |
| 10 | 0.017 µM |

Ischemia-Induced Arrhythmias in Anaesthetized Rats:

Male Charles Foster rats (220–260 g) were anaesthetized with Pentobarbitone sodium. Animals were artificially ventilated. Blood pressure was recorded through carotid artery. Thoracotomy was performed to expose the heart. Left Anterior Descending (LAD) coronary artery was identified. Test compound was administered either orally 10 minutes before anaesthesia (40 minutes before LAD artery ligation) or intravenously (5 minutes before LAD artery ligation). Resulting arrhythmias during the 15 minute period of ligation were recorded and analyzed according to Lambeth Convention (Walker M. J. A, et al, 1988, Cardiovascular Research, 22, 447–455). Antiarrhythmic effect of the test compound was expressed as dose dependent inhibition of the duration of Ventricular Tachycardia (VT) and Ventricular Fibrillation (VF).

TABLE 6

| Compound No. | Dose mg/kg | VT Percent inhibition | VF Percent inhibition |
|---|---|---|---|
| Oral Administration: | | | |
| 2 | 1 | 26 ± 0 (n = 11) | 68 ± 19 (n = 10) |
|   | 3 | 31 ± 21 (n = 13) | 93 ± 5 (n = 13) |
|   | 10 | 73 ± 8 (n = 13) | 00 ± 0 (n = 13) |
| 10 | 0.1 | 32 ± 12 (n = 7) | NP* |
|   | 0.3 | 69 ± 11 (n = 6) | 84 ± 11 (n = 8) |
|   | 1.0 | 67 ± 11 (n = 8) | 100 ± 0 (n = 8) |
| Intravenous Administration: | | | |
| 2 | 0.1 | 57 ± 17 (n = 9) | 100 ± 0 (n = 9) |
|   | 0.3 | 90 ± 3 (n = 12) | 100 ± 0 (n = 12) |
|   | 1.0 | 98 ± 1 (n = 12) | 100 ± 0 (n = 12) |
| 10 | 0.1 | 20 ± 24 (n = 8) | 100 ± 0 (n = 8) |
|   | 0.3 | 81 ± 8 (n = 8) | 100 ± 0 (n = 9) |
|   | 1.0 | 97 ± 1 (n = 8) | 100 ± 0 (n = 8) |

*NP - No protection

Myocardial Infarction in the Anaesthetized Rat:

Rats were prepared as in earlier experiments. Compounds were administered intravenously 5 minutes before ligation. The experiment consisted of one hour of ligation followed by one hour of reperfusion. Myocardial infarction was assessed by double dye technique using Evans blue and 2,3,5-Triphenyltetrazolium to identify area at risk and area of infarction respectively. Extent of infarction was expressed as a percent of area at risk. (Simpson et al, 1987, Circulation Research, 60, 666–673)

TABLE 7

| Compound No. | Protection against infarction |
|---|---|
| 2 | 17% (n = 8) |
| 10 | 68% (n = 8) |

We claim:
1. A compound of formula I

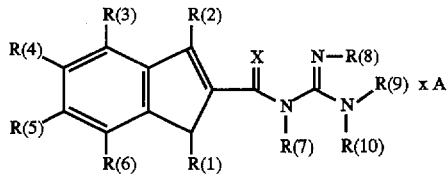

wherein
R(1) and R(2) are
hydrogen, alkyl having 1, 2, 3, 4, 5, 6, 7, 8, 9 or 10 carbon atoms/cycloalkyl having 3, 4, 5 or 6 carbon atoms, O-alkyl having 1, 2, 3 or 4 carbon atoms, O—C(=O)-alkyl having 1, 2, 3 or 4 carbon atoms, $C_mH_{2m}$-NR(12) R(13), wherein
R(12) and R(13) are independently from each other hydrogen or alkyl having 1, 2, 3 or 4 carbon atoms; m is zero, 1, 2, 3 or 4;
NH—C(=O)—NH$_2$, C(=O)-O-alkyl having 1, 2, 3 or 4 carbon atoms, C(=O)—NH$_2$, C(=O)-NH-alkyl having 1, 2, 3 or 4 carbon atoms, C(=))-N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3, or 4 carbon atoms in the alkyl group, alkenyl-aryl having 2, 3, 4, 5, 6, 7, 8, 9, or 10 carbon atoms in the alkenyl group, alkynyl-aryl having 2, 3, 4, 5, 6, 7, 8, 9, or 10 carbon atoms in the alkynyl group, $C_1$-$C_4$-alkyl-substituted-aryl, $C_1$-$C_4$-alkyl-heteroaryl, $C_1$-$C_4$-alkenyl-heteroaryl, aminoalkyl-aryl having 1, 2, 3, or 4 carbon atoms in the alkyl group, substituted-aryl, heteroaryl or substituted heteroaryl;
R(3), R(4), R(5) and R(6) are
hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogens, OH, aryl, substituted aryl, heteroaryl, substituted heteroaryl, O-lower alkyl, O-aryl, O-lower alkyl aryl, O-substituted aryl, O-lower alkyl-substituted aryl, O—C(=O)-$C_1$-$C_4$-alkyl-aryl, O—C(=O)—NH-$C_1$-$C_4$-alkyl, O—C(=O)-N ($C_1$-$C_4$-alkyl)$_2$, NO$_2$, CN, CF$_3$, NH$_2$, NH—C(=O)-$C_1$-$C_4$-alkyl, NH—C(=O)-NH$_2$, COOH, C(=O)—O-$C_1$-$C_4$-alkyl, C(=O)-NH$_2$, C(=O)—NH-$C_1$-$C_4$-alkyl, C(=O)—N($C_1$-$C_4$-alkyl)$_2$, $C_1$-$C_4$-COOH, $C_1$-$C_4$-alkyl-C(=O)—O-$C_1$-$C_4$-alkyl, SO$_3$H, SO$_2$alkyl, SO$_2$-alkylaryl, SO$_2$-N-(alkyl)$_2$, SO$_2$-N (alkyl) (alkylaryl), C(=O)-R(11), $C_1$-$C_{10}$-alkyl-C(=O)-R(11), $C_2$-$C_{10}$-alkenyl-C(=O)-R(11), $C_2$-$C_{10}$-alkynyl-C(=O)-R(11), NH—C(=O)-$C_1$-$C_{10}$-alkyl-C(=O)-R(11), O-$C_1$-$C_{11}$-alkyl-C(=O)-R(11), wherein R(11) is
$C_1$-$C_4$-alkyl, $C_1$-$C_4$-alkynyl, aryl substituted aryl, NH$_2$, NH-$C_1$-$C_4$-alkyl, N-($C_1$-$C_4$-alkyl)$_2$, SO$_3$H, SO$_2$alkyl, SO$_2$-alkylaryl, SO$_2$-N-(alkyl)$_2$, SO$_2$-N (alkyl) (alkylaryl);
X is O, S or NH;

R(7), R(8), R(9) and R(10) are
hydrogen, alkyl, cycloalkyl, aryl, alkylaryl;
or
R(8) and R(9)
together are a part of a 5, 6 or 7-membered heterocyclic ring;
A is absent, or a nontoxic organic or mineral acid.
2. A compound as claimed in claim 1 of the formula II

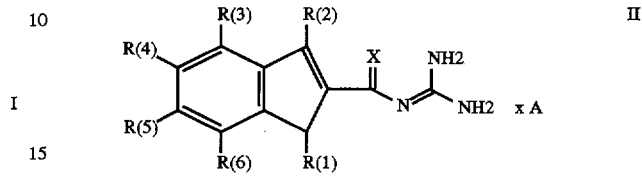

wherein
R(1) is hydrogen, $C_1$-$C_4$-alkyl, NR(12)R(13), wherein
R(12) and R(13) are independently from each other hydrogen or alkyl having 1, 2, 3 or 4 carbon atoms, $C_1$-$C_4$-alkyl-NH$_2$, aryl-alkyl-NH$_2$, O-alkyl, C(=O)-NH (lower alkyl), C(=O)-N(lower alkyl)$_2$, C(=O)-O-lower alkyl, substituted alkyl, aryl, substituted aryl;
R(2) is hydrogen, $C_1$-$C_4$-alkyl, $C_1$-$C_4$-alkyl-NH$_2$, aryl-alkyl-NH$_2$, substituted alkyl, aryl, substituted aryl;
R(3), R(4), R(5) and R(6) are
F, Cl, Br, I, O, O-lower alkyl, O-aryl, O-lower alkyl-aryl, O-substituted aryl, O-lower alkyl-substituted aryl, COOH, C(=O)-O-lower alkyl, CN, CF$_3$, NH$_2$, NH-lower alkyl, N(lower alkyl)$_2$, O-lower alkyl-NH$_2$, O-lower alkyl-NH(lower alkyl), O-lower alkyl-N (lower alkyl)$_2$, SO$_2$-lower alkyl, SO$_3$H, SO$_2$-NH$_2$, SO$_2$-NH-lower alkyl, SO$_2$-N(lower alkyl)$_2$, pyridyl, thienyl, furyl, quinyl and isoquinyl, or these heteroaryls substituted by 1–3 substituents selected from the group consisting of
F, Cl, Br, I, OH, NH$_2$, O-lower alkyl, O-lower alkyl-aryl, COOH, C(=O)-O-lower alkyl, CN, NH-lower alkyl, N(lower alkyl)$_2$ SO$_3$H, SO$_2$-NH$_2$, SO$_2$-NH-lower alkyl, and SO$_2$-N(lower alkyl)$_2$;
X is O, S or
A is absent, or a nontoxic organic or mineral acid.
3. A compound of formula II as claimed in claim 2, wherein
R(1) is hydrogen, $C_1$-$C_4$-alkyl, NR(12)R(13) wherein
R(12) and R(13) are independently from each other hydrogen or alkyl having 1, 2, 3 or 4 carbon atoms, $C_1$-$C_4$-alkyl-NH$_2$, aryl-alkyl-NH$_2$, O-alkyl, C(=O)-NH (lower alkyl), C(=O)-N(lower alkyl)$_2$, C(=O)-O-lower alkyl, substituted alkyl, aryl, substituted aryl;
R(2) is hydrogen, $C_1$-$C_4$-alkyl, $C_1$-$C_4$-alkyl-NH$_2$, aryl-alkyl-NH$_2$, substituted alkyl, aryl, substituted aryl;
R(3), R(4), R(5) and R(6) are
F, Cl, Br, I, OH, O-lower alkyl, O-aryl, O-lower alkyl-aryl, O-substituted aryl, O-lower alkyl-substituted aryl, COOH, C(=O)-O-lower alkyl, CN, CF$_3$, NH$_2$, NH-lower alkyl, N(lower alkyl)$_2$, O-lower alkyl-NH$_2$, O-lower alkyl-NH-(lower alkyl), O-lower alkyl-N (lower alkyl)$_2$, SO$_2$-lower alkyl, SO$_3$H, SO$_2$NH$_2$, SO$_2$-NH-lower alkyl, SO$_2$-N(lower alkyl)$_2$, pyridyl, thienyl, furyl, quinyl and isoquinyl, or these heteroaryls substituted by 1–3 substituents selected from the group consisting of
F, Cl, Br, I, OH, NH$_2$, O-lower alkyl, O-lower alkyl-aryl, COOH, C(=O)-O-lower alkyl, CN, NH-lower alkyl, N(lower alkyl)$_2$, SO$_3$H, SO$_2$-NH$_2$, SO$_2$-NH-lower alkyl, and SO$_2$-N(lower alkyl)$_2$;

X is O;

A is absent, or a nontoxic organic or mineral acid.

4. A process for the preparation of a compound of formula I as claimed in claim 1 which comprises a) reacting a compound of formula VI

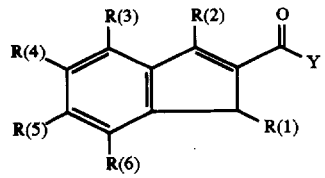

in which R(1), R(2), R(3), R(4), R(5) and R(6) are defined as claim 1, and in which Y is a leaving group selected from the group consisting of —O-(C₁-C₄)-alkyl, halogen and imidazolyl, with a guanidine of formula VII

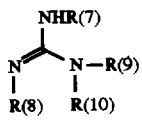

in which R(7), R(8), R(9) and R(10) are defined as in claim 1, and optionally converting the product into a pharmaceutically tolerated salt.

5. A method for the treatment of cardiac arrhythmias comprising administering an effective amount of a compound of formula I as claimed in claim 1.

6. A method for the treatment of prophylaxis of cardiac infarction comprising administering an effective amount of a compound of formula I as claimed in claim 1.

7. A method for the treatment of angina pectoris comprising administering an effective amount of a compound of formula I as claimed in claim 1.

8. A method for the treatment of prophylaxis of ischemic states of the heart comprising administering an effective amount of a compound of formula I as claimed in claim 1.

9. A method for the treatment of prophylaxis of ischemic states of the peripheral and central nervous system and of apoplexy comprising administering an effective amount of a compound of formula I as claimed in claim 1.

10. A method for the treatment of prophylaxis of ischemic states of peripheral organs and extremities comprising administering an effective amount of a compound of formula as claimed in claim 1.

11. A method for the treatment of shock states comprising administering an effective amount of a compound of formula I as claimed in claim 1.

12. A method of protecting organs during surgical operations and organ transplants comprising administering an effective amount of a compound of formula I as claimed in claim 1.

13. A method of preserving or storing transplants for surgical measures, comprising administering an effective amount of a compound of formula I as claimed in claim 1.

14. A method for the treatment of a disease in which cell proliferation is a primary or secondary cause comprising administering an effective amount of a compound of formula I as claimed in claim 1.

15. A method for the treatment of a delayed diabetic complication, cancer disease, fibrotic disease, pulmonary fibrosis, hepatic fibrosis or renal fibrosis, or prostate hyperplasia comprising administering an effective amount of a compound of formula I as claimed in claim 1.

16. A method of investigating the inhibition of cellular sodium proton antiport comprising administering an effective amount of a compound of formula I as claimed in claim 1 as a diagnostic agent.

17. A pharmaceutical composition comprising an effective amount of a compound of formula I as claimed in claim 1.

* * * * *